US010159467B2

(12) United States Patent
Blanz et al.

(10) Patent No.: US 10,159,467 B2
(45) Date of Patent: Dec. 25, 2018

(54) METHOD FOR SEAM ELIMINATION AND RECONSTRUCTION OF COPLANAR IMAGES FROM INTRAVASCULAR ULTRASONIC DATA

(71) Applicant: Volcano Corporation, San Diego, CA (US)

(72) Inventors: Wolf-Ekkehard Blanz, San Jose, CA (US); Jerome Mai, Seattle, WA (US)

(73) Assignee: VOLCANO CORPORATION, San Diego, CA (US)

( * ) Notice: Subject to any disclaimer, the term of this patent is extended or adjusted under 35 U.S.C. 154(b) by 1072 days.

(21) Appl. No.: 13/958,409

(22) Filed: Aug. 2, 2013

(65) Prior Publication Data

US 2014/0039308 A1 Feb. 6, 2014

Related U.S. Application Data

(60) Provisional application No. 61/678,968, filed on Aug. 2, 2012.

(51) Int. Cl.
| *A61B 8/00* | (2006.01) |
| *A61B 8/08* | (2006.01) |
| *A61B 6/00* | (2006.01) |
| *A61B 8/12* | (2006.01) |
| *A61B 5/00* | (2006.01) |

(52) U.S. Cl.
CPC ............. *A61B 8/52* (2013.01); *A61B 5/0066* (2013.01); *A61B 6/52* (2013.01); *A61B 8/12* (2013.01); *A61B 8/523* (2013.01)

(58) Field of Classification Search
None
See application file for complete search history.

(56) References Cited

U.S. PATENT DOCUMENTS

| 6,148,095 | A | * | 11/2000 | Prause | ................... | G06T 17/00 |
| | | | | | | 128/916 |
| 2004/0147837 | A1 | | 7/2004 | Macaulay et al. | | |
| 2006/0241484 | A1 | | 10/2006 | Horiike et al. | | |
| 2007/0016029 | A1 | * | 1/2007 | Donaldson | ............. | A61B 8/469 |
| | | | | | | 600/437 |
| 2008/0287795 | A1 | * | 11/2008 | Klingensmith | .... | A61B 5/02007 |
| | | | | | | 600/443 |

(Continued)

FOREIGN PATENT DOCUMENTS

WO WO 2011-053931 A2 5/2011

OTHER PUBLICATIONS

International Search Report and Written Opinion received in Patent Cooperation Treaty Application No. PCT/US2013/053016, dated Nov. 22, 2013, 11 pages.

*Primary Examiner* — Christopher Cook (57) ABSTRACT

Methods, devices, and systems for providing seamless, co-planar intravascular ultrasound (IVUS) images are provided. In some embodiments, the methods include projecting a first A-scan line from a distal frame onto a reconstruction plane that extends perpendicular to an imaging axis, projecting a second A-scan line parallel to the first A-scan line from the proximal frame on the reconstruction plane; and determining a grayscale value of a point on the reconstruction plane by a weighted average of the first A-scan line and the second A-scan line.

19 Claims, 7 Drawing Sheets

(56) References Cited

U.S. PATENT DOCUMENTS

| | | | |
|---|---|---|---|
| 2012/0059253 A1* | 3/2012 | Wang | A61B 6/00 600/427 |
| 2012/0130243 A1 | 5/2012 | Balocco et al. | |
| 2012/0130247 A1 | 5/2012 | Waters et al. | |
| 2012/0170848 A1* | 7/2012 | Kemp | G06T 5/50 382/195 |

* cited by examiner

METHOD FOR SEAM ELIMINATION AND RECONSTRUCTION OF COPLANAR IMAGES FROM INTRAVASCULAR ULTRASONIC DATA

CROSS REFERENCE TO RELATED APPLICATION

The present application claims priority to and the benefit of U.S. Provisional Patent Application No. 61/678,968, filed Aug. 2, 2012, which is hereby incorporated by reference herein in its entirety.

TECHNICAL FIELD

The present disclosure relates generally to intravascular ultrasound (IVUS) imaging inside the living body and, in particular, to a method for reconstructing coplanar images from an IVUS scanning system.

BACKGROUND

Intravascular ultrasound (IVUS) imaging is widely used in interventional cardiology as a diagnostic tool for a diseased vessel, such as an artery, within the human body to determine the need for treatment, to guide the intervention and/or to assess its effectiveness. IVUS imaging uses ultrasound echoes to create an image of the vessel of interest. The ultrasound waves pass easily through most tissues and blood, but they are partially reflected from discontinuities arising from tissue structures (such as the various layers of the vessel wall), red blood cells, and other features of interest. The IVUS imaging system, which is connected to the IVUS catheter by way of a patient interface module (PIM), processes the received ultrasound echoes to produce a cross-sectional image of the vessel where the catheter is placed. The image cross-section in a typical IVUS scan is formed of a plurality of radial A-scan lines. Each A-scan line results from echoes collected from an ultrasound signal emitted by the catheter. The ultrasound signal is a pulse forming a beam propagating radially outwards from the intravascular device towards the blood vessel, which defines the longitudinal direction.

Conventional IVUS imaging methods produce images while a transducer in the catheter head moves through a blood vessel during a scan (e.g., during a pullback). The ultrasound signal is typically collected over a small angular sector of the cross-sectional image one at a time, rather than simultaneously around 360 degrees. Thus, radial A-scan lines are not necessarily co-planar as they are collected at different longitudinal positions as the catheter moves along the blood vessel. Typical IVUS images are displayed as if the A-scans comprising a 360° rotation about the longitudinal direction are co-planar even though they are not. The result is a discontinuity between the first (0°) and the last (360°) radial scans because of the different longitudinal positions between the first and last radial beams. This discontinuity is called a 'seam' and is typically arbitrarily placed either at the 3 o'clock or the 12 o'clock position in an IVUS image. The seam is especially visible if image was acquired from a very fast pullback, or around tissues with high motion. The seam between the 0° and the 360° scans not only distorts the image, but it displays non-coplanar data points as if collected at a plane orthogonal to the longitudinal direction of the blood vessel. The difference of longitudinal position between two consecutive radial A-scans, and between the points along an A-scan being not perpendicular to the longitudinal direction is sometimes neglected because it may be visually unnoticed for relatively small pullback speeds $v_z$. In reality, collected data points correspond to a twisted band (or helical plane) bounded on the outside by a helix (or cork screw) and on the inside by a longitudinal axis extending along the blood vessel. Inaccurate imaging becomes more pronounced as catheter withdrawal speeds are increased, as the difference in longitudinal distance lengthens between the beginning (0°) and end (360°) of the IVUS image.

Accordingly, there remains a need for methods of scan conversion and associated systems and devices that correct the seams resulting from non-coplanar radial A-scan lines in IVUS imaging.

SUMMARY

In some embodiments, methods for reconstructing coplanar intravascular ultrasound (IVUS) images are provided. In some embodiments, the method includes: obtaining IVUS scan data for at least a proximal frame and a distal frame generated during an IVUS pullback through a vessel, wherein the IVUS pullback extends along a longitudinal axis and has a starting point and an ending point, the ending point being proximal of the starting point; selecting a position along the longitudinal axis between the starting point and the ending point; projecting a first A-scan line from the distal frame on a reconstruction plane that intersects the longitudinal axis at the selected position; projecting a second A-scan line parallel to the first A-scan line from the proximal frame on the reconstruction plane; and determining a grayscale value of a point on the reconstruction plane by a weighted average of the first A-scan line and the second A-scan line. In one aspect, the reconstruction plane extends perpendicular to the longitudinal axis.

In other embodiments, the method includes: obtaining IVUS scan data for at least a distal frame, middle frame, and a proximal frame generated during an IVUS pullback through a vessel, wherein the IVUS pullback extends along a longitudinal axis and has a starting point and an ending point, the ending point being proximal of the starting point; selecting a position along the longitudinal axis between the starting point and the ending point; projecting a first A-scan line from the middle frame on a reconstruction plane that intersects the longitudinal axis at the selected position; projecting a second A-scan line parallel to the first A-scan line onto the reconstruction plane, wherein the second A-scan line is from the proximal frame when the reconstruction plane is proximal to the first A-scan line and wherein the second A-scan line is from the distal frame when the reconstruction plane is distal to the first A-scan line; and determining a grayscale value of a point on the reconstruction plane by a weighted average of the first A-scan line and the second A-scan line. In one aspect, the reconstruction plane extends perpendicular to the longitudinal axis.

Further, systems for reconstructing coplanar intravascular ultrasound (IVUS) images are also provided. In some embodiments, the system comprises: an intravascular imaging device having at least one imaging element; a processing system in communication with the intravascular imaging device, the processing system configured to: obtain IVUS scan data from the imaging catheter for at least a proximal frame and a distal frame generated during an IVUS pullback through a vessel, wherein the IVUS pullback extends along a longitudinal axis and has a starting point and an ending point, the ending point being proximal of the starting point; and display on a display a seamless, co-planar image for a reconstruction plane at a position between the starting point and the ending point. In a further feature, the reconstruction plane extends perpendicular to the longitudinal axis.

These and other embodiments of the present invention will be described in further detail below with reference to the following drawings.

BRIEF DESCRIPTION OF THE DRAWINGS

In the figures, elements having the same reference number have the same or similar functions.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

According to embodiments disclosed herein, methods to provide seamless, continuous image in an intravascular ultrasound (IVUS) imaging system are provided. Moreover, the method described in this disclosure is may be applicable to Optical Coherent Tomography (OCT) where pullback speeds are often significantly larger than they are in IVUS or rotational IVUS. The physics behind image formation in OCT are radically different from IVUS; however, image acquisition in OCT is plagued by the same set of problems introduced by a non-stationary receiver that is moving in z-direction during image acquisition. Because of the very high pullback speeds used in OCT, a desirable plane reconstruction method in this case is the one that accounts for displacement in z-direction during the acquisition of the equivalent of a radial beam.

Embodiments as disclosed herein improve quality and fidelity of intravascular ultrasonic images by displaying measured echoes as coplanar data rather than data obtained from a helix-bounded band. Thus, IVUS imaging methods according to some embodiments disclosed herein provide continuous tissue images with no visible seam or artifact. Seamless images displayed in a planar fashion on a screen provide improved information about the state of a vessel to clinicians, which can lead to better diagnosis and, therefore, better treatment of the patient.

Figure 1:
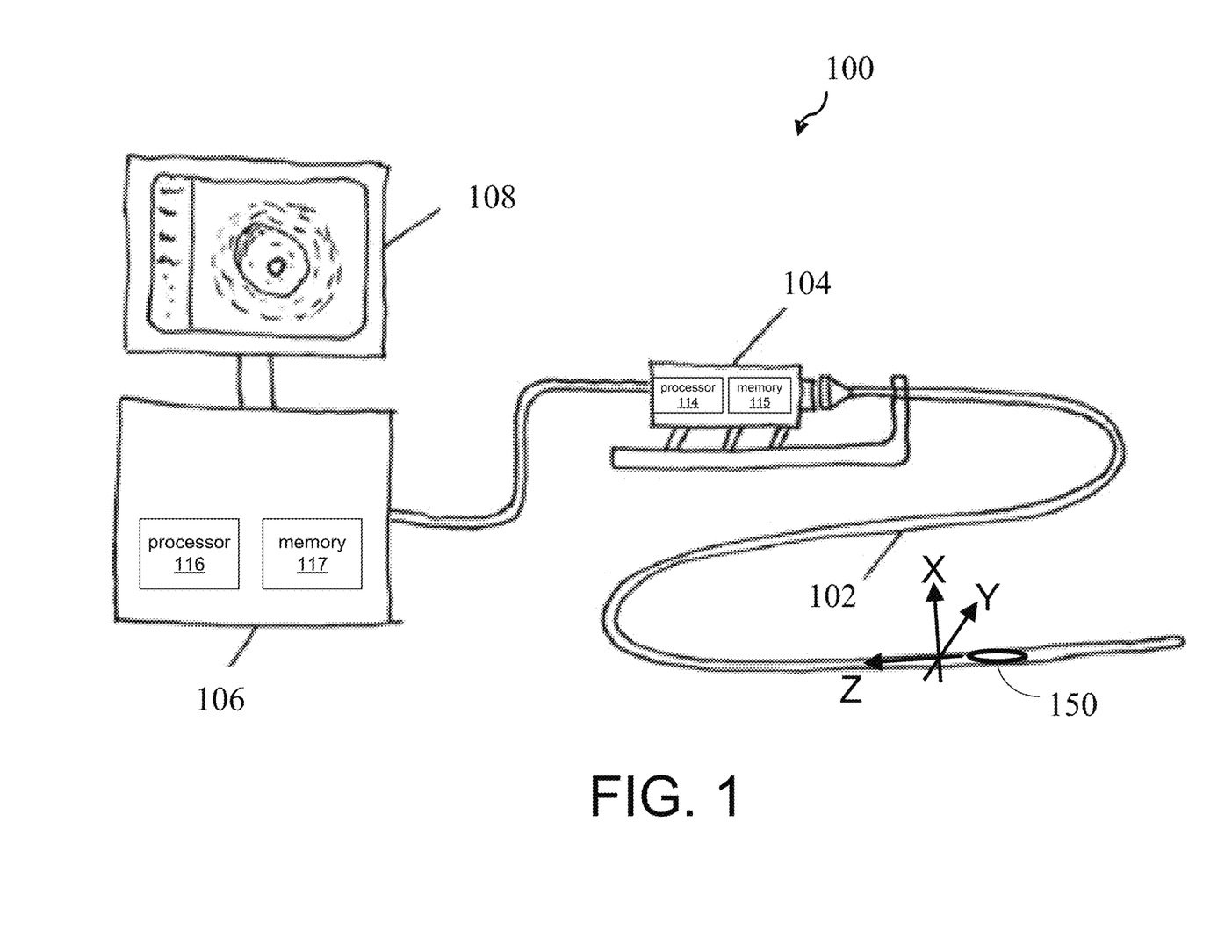
FIG. 1 is a diagrammatic schematic view of an imaging system according to an embodiment of the present disclosure.

FIG. 1 shows an IVUS imaging system 100 according to an embodiment of the present disclosure. In some embodiments of the present disclosure, IVUS imaging system 100 may be a rotational IVUS imaging system or an array IVUS imaging system. In that regard, the main components of the IVUS imaging system are an IVUS catheter 102, a patient interface module (PIM) 104, an IVUS console or processing system 106, and a monitor 108 to display the IVUS images generated by the IVUS console 106. Catheter 102 may include an ultrasound transducer 150, according to some embodiments. PIM 104 implements the appropriate interface specifications to support catheter 102. According to some embodiments, PIM 104 generates a sequence of transmit trigger signals and control waveforms to regulate the operation of ultrasound transducer 150. In embodiments where ultrasound transducer 150 is a rotating transducer, a rotational speed $\omega_m$ (revolutions/minute) indicates the speed of rotation of the transducer 150 about the Z axis. In FIG. 1, IVUS console 106 includes console processor circuit 116 and console memory circuit 117, while PIM 104 includes PIM processor circuit 114 and PIM memory circuit 115.

In FIG. 1, the XYZ Cartesian system has the z-axis oriented on a longitudinal direction along catheter 102, which is inserted along the blood vessel during use. Accordingly, in some instances the z-axis is oriented along both the catheter 102 and the blood vessel. The z-axis in FIG. 1 is oriented such that the value of the z-coordinate increases in the proximal direction to IVUS system 100. In embodiments where ultrasound transducer 150 is an array transducer, a rotational speed $\omega_m$ indicates the speed at which an ultrasound beam is electronically stepped and steered along A-scan lines in the XY plane, completing a 360° rotation about the Z axis in the XY plane. One of ordinary skill will recognize that the particular choice of coordinate system is not limiting. Any axis may be arbitrarily chosen to identify the longitudinal direction for the IVUS scan along the blood vessel direction. Furthermore, any other coordinate choice may be used to identify a plane perpendicular to the longitudinal direction, without limiting the general concept disclosed herein. Moreover, the particular orientation of the XYZ coordinate system may change as catheter 102 is displaced along a longitudinal direction in a blood vessel. Axes and coordinates referred hereinafter will be consistent with the Cartesian system described in FIG. 1, without limiting embodiments disclosed herein.

Ultrasound transducer 150 transmits ultrasound signals from trigger signals received from PIM 104 towards the tissue of interest. Ultrasound transducer 150 also converts echo signals received from the tissue into electrical signals to be processed by PIM 104 and IVUS console 106. PIM 104 also supplies high- and low-voltage DC power supplies to support operation of rotational IVUS catheter 102. In some embodiments, PIM 104 delivers a DC voltage to circuitry driving transducer 150 across a rotational interface.

Figure 2:
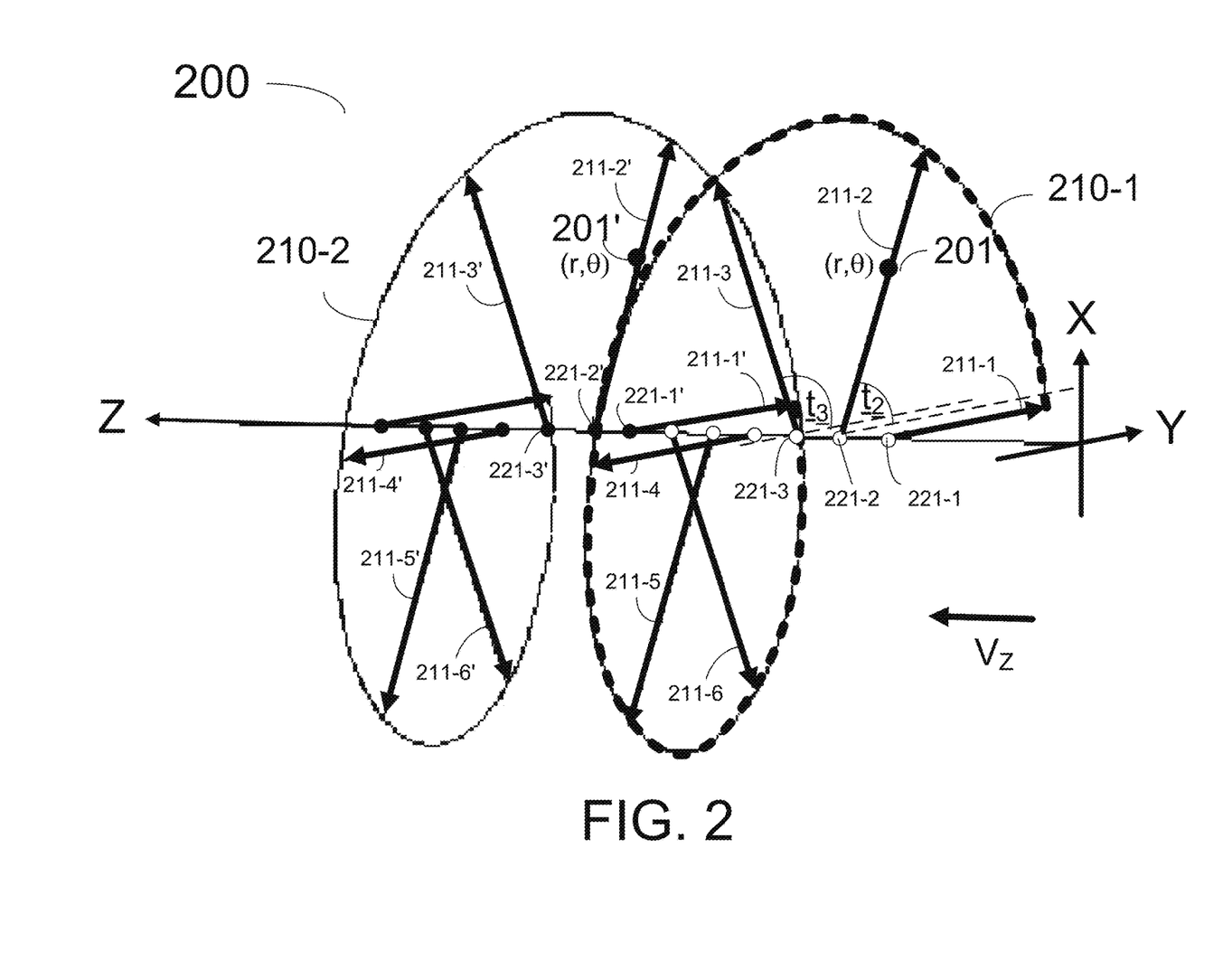
FIG. 2 is a graphical representation of an IVUS scan according to an embodiment of the present disclosure.

FIG. 2 is a schematic view of an IVUS scan 200 according to an embodiment of the present disclosure. Scan 200 includes at least two complete rotations or frames 210-1 and 210-2 of the ultrasound beam about a longitudinal direction (Z). Frame 210-1 includes A-scan lines 211-1 through 211-6, collectively referred to as A-scan lines 211. Frame 210-2 includes A-scan lines 211-1' through 211-6', collectively referred to as A-scan lines 211'. Each of A-scan lines 211 or 211' includes a plurality of discrete data points 201 corresponding to measurements of an echo signal by IVUS imaging system 100. Each of A-scan lines 211 in a distal frame 210-1 has an initial point at the longitudinal line 221-1 through 221-6, collectively referred as A-scan origin points 221. Each of A-scan lines 211' in a proximal frame 210-2 has an initial point at the longitudinal line 221-1' through 221-6', collectively referred as A-scan origin points 221'. A-scan origin points 221 and 221' correspond to polar coordinates r=0 and θ=0. Polar coordinates are convenient for the description of A-scan lines in scan 200 because each A-scan line 211 or 211' may be defined by a single value of an angle θ about the z-axis. Radial coordinate 'r' measures the distance between a sampling point 201 and the z-axis. Angle θ may be measured relative to the Y-axis in FIG. 2. For example, as illustrated in FIG. 2, angle $t_2$ may define A-scan line 211-2, and angle $t_3$ may define A-scan line 211-3. Furthermore, angles $t_4$ through $t_6$ (not shown in FIG. 2 for clarity) may define A-scan lines 211-4 through 211-6. Similarly, angles $t_2'$ through $t_6'$ (not shown in FIG. 2 for clarity) may define A-scan lines 211-2' through 211-6'. Accordingly, angles $t_1=0°$ and $t_2=0°$ (not shown for clarity) may define a first A-scan line in frame 210-1, and a first A-scan line in frame 210-2, respectively.

Conventional IVUS imaging is produced by spinning or steering an ultrasound beam produced by a catheter head at $\omega_m$ revolutions per minute. As the ultrasound beam rotates and the echo signal is collected, the catheter head is pulled back at an approximate speed $v_z$ through a blood vessel. Ultrasound pulses are sent by transducer 150 in the catheter head at defined time intervals $\Delta t_\theta$, for a total of nθ times per rotation or frame, thus producing $n_\theta$ A-scan lines per revolution. For example, for sake of clarity only 6 scan lines per revolution (or frame) are shown in FIG. 2. However, the number $n_\theta$ is not limiting. In some embodiments, $n_\theta$ is 64, 128, 256, 512, or larger. In embodiments using ultrasound transducer arrays, the number of scan lines may be related to the number of elements in the array. The received echo signals are sampled at time intervals of $\Delta t_r$, producing $n_r$ samples per radial beam. In some embodiments, $\Delta t_r$ may be $2.5 \times 10^{-8}$ s. Thus, the data collected is in polar coordinates, each data point having a radial and an angular coordinate. In some embodiments the data is converted into Cartesian x/y coordinates or 'raster scan' mode, for clinical use on a CRT or at a screen monitor. In a monitor such as monitor 108, each pixel is characterized by an x/y coordinates on the screen. The process of converting the polar coordinates of the raw data from transducer 150 to the Cartesian raster scan data for display 108 is called scan conversion. For each raster point (pixel) in a display, its x/y coordinates' corresponding polar coordinates are determined. If polar coordinates of the raster point correspond to a measurement point 201, the measured intensity of point 201 is directly used as a grayscale. If there is no measurement point 201 at the precise location of the raster point, a grayscale value interpolated between neighboring measurement points in polar coordinates is used as the intensity of that pixel on the raster scan.

Embodiments consistent with the present disclosure use non-coplanar image points 201 and 201' acquired during frames 210-1 and 210-2, respectively, to provide coplanar images. In some embodiments, the plane of the resulting images is perpendicular to the z-axis in FIG. 2. Accordingly, in some embodiments a function $f_z(i_r; i_\theta; i_z)$ restores the correct z-position for each acquired data point 201. Data point 201 may be determined by indices $i_r$, $i_\theta$, and $i_z$, which are integer numbers. Indices ($i_r$, $i_\theta$, $i_z$) represent the order in which data point 201 is collected in the IVUS scan procedure. For example, $i_r$ may represent the order of data point 201 along an A-scan 211, starting at the z-axis, counting radially outwards. Thus, in some embodiments index $i_r$ is related to a radius of data point 201 to the center of the IVUS catheter 102, along a line formed by A-scan 211. In some embodiments, a second index $i_\theta$ may represent a specific A-scan line 211 within a frame such as frame 210-1. Thus, index $i_\theta$ is related to an angle θ of an A-scan line, such as angle $t_2$ or $t_3$. For example, index $i_\theta$ includes values from 1 through 6, in FIG. 2. Further, in some embodiments index $i_z$ may represent the position of A-scan lines 211-1 and 211-1' along the z-direction ($i_z$), such as given at points 221-1 and 221-1'. In some embodiments, index $i_z$ is associated to a specific frame in an IVUS scan. For example, frames 210-1 and 210-2 may be associated to consecutive values of an $i_z$ index, according to some embodiments.

Thus, according to some embodiments function $f_z$ includes three integer indices determining data point 201. Function $f_z$ provides the value of a coordinate of point 201 along the z-axis. This allows reconstruction of image data in arbitrary planes perpendicular to the z-axis, using interpolation between data points 201 of neighboring frames with given $i_r$, $i_\theta$, and $i_z$ indices. In some embodiments, a specific reconstruction plane is perpendicular to the longitudinal direction and has a specific z-image position (i.e., position along the z-axis). Thus, the value used for image reconstruction in the reconstruction plane is an interpolation between a data point 201 having an $f_z$ value lower than the z-image position, and a data point 201 having an $f_z$ higher than the z-image position.

Forming function $f_z$ may include forming a function $f_1(i_z)$ defined as $$f_1(i_z) := f_z(i_r=0; i_\theta=0; i_z),$$

which is the function that provides the z-coordinate of the beginning of each frame, given its frame index $i_z$. For example, function $f_1$ determines the z-coordinate of a first point in A-scan line 211-1, such as point 221-1. Since the transducer is rotating continuously (or elements of a transducer array are being fired to step around 360°), the time between the start of two adjacent frames (such as 210-1 and 210-2) is the time it takes for one full revolution of the ultrasound beam about the z-axis, which is $$\Delta t_z = \frac{1}{\omega_m} \cdot 60 \frac{s}{\min}$$

Some embodiments include a rotational speed $\omega_s$ as the number of revolutions per second, i.e.

$$\omega_s = \omega_m \cdot \frac{\min}{60s}$$

After $i_z$-complete revolutions moving at speed $v_z$, the displacement in z-direction of A-scan line 211 is $$f_1(i_z) = i_z \cdot v_z \cdot \Delta t_z$$
$$= i_z \cdot \frac{v_z}{\omega_s}$$

In some embodiments, forming function $f_z$ may also include forming a function $f_2$ $(i_\theta; i_z)$ as $$f_2(i_{74}; i_z) := f_z(i_r=0; i_\theta; i_z).$$

Function $f_2$ provides the z-coordinate of points 221 in A-scan lines 211 given a beam index $i_\theta$ and a frame index $i_z$. In some embodiments, function $f_2$ is obtained adding the z-displacement after completion of '$i_\theta$' A-scan lines 211 to the value in function $f_1$. If there are $n_\theta$ radial beams per revolution, then the time it takes to complete one of them is $$\Delta t_\theta = \frac{1}{\omega_s n_\theta}$$

The displacement along the z-direction for $i_\theta$ A-scan lines 210 is $i_\theta \cdot v_z \cdot \Delta t_\theta$. Hence, in some embodiments function $f_2$ is $$f_2(i_\theta; i_z) = f_1(i_z) + i_\theta \cdot v_z \cdot \Delta t_\theta$$

$$= f_1(i_z) + v_z \cdot \frac{1}{\omega_s} \cdot \frac{i_\theta}{n_\theta}$$

$$= \frac{v_z}{\omega_s} \cdot \left(i_z + \frac{i_\theta}{n_\theta}\right)$$

In some embodiments, forming function $f_z$ includes adding to function $f_2$ the z-displacement due to the time interval between subsequent samplings along the radial direction. When a time interval between subsequent samples along a radial line is $\Delta t_r$, an additional z-displacement for $i_r$ samples may be $i_r \cdot v_z \cdot \Delta t_r$. Thus, in some embodiments a function $f_z$ may be formed as $$f_z(i_r; i_\theta; i_z) = f_2(i_\theta; i_z) + i_r \cdot v_z \cdot \Delta t_r \quad (1)$$

$$= \frac{v_z}{\omega_s} \cdot \left(i_z + \frac{i_\theta}{n_\theta}\right) + i_r \cdot v_z \cdot \Delta t_r$$

$$= v_z \cdot \left(\frac{1}{\omega_s} \cdot \left(i_z + \frac{i_\theta}{n_\theta}\right) + i_r \cdot \Delta t_r\right)$$

Function $f_z$ provides an accurate z-value to sampling point 201 defined by indices $(i_r, i_\theta, i_z)$. Function $f_z$ may be used to interpolate data for an arbitrary reconstruction plane between data points 201 having subsequent $i_z$ index and the same $i_r$, $i_\theta$ indices. In some embodiments, forming function $f_z$ includes determining the pullback speed $v_z$, the rotational speed of transducer 150 ($\omega_m$ or $\omega_s$), the number of radial beams per frame $n_\theta$, and the time sampling interval between data acquisitions along the radial direction, $\Delta t_r$. In some embodiments, pullback velocity $v_z$, may be constant, or approximately constant. This may be the case in embodiments where the pullback of catheter 102 is automatically performed by a machine. In some embodiments of an IVUS imaging system the catheter pullback may be manual, and velocity $v_z$ may not be constant. In such embodiments, pullback speed $v_z$ may not be known precisely. However, when interpolating data from consecutive frames 210-1 and 210-2 to reconstruct an image plane including point 221-1', $v_z$ can be considered constant between the two frames locally. In some embodiments, the specific value of $v_z$ is not limiting, and may not be needed for coplanar image reconstruction. The use of function $f_z$ to form a coplanar reconstruction image from frames 210-1 and 210-2 is described in detail in relation to FIG. 3, below.

Figure 3:
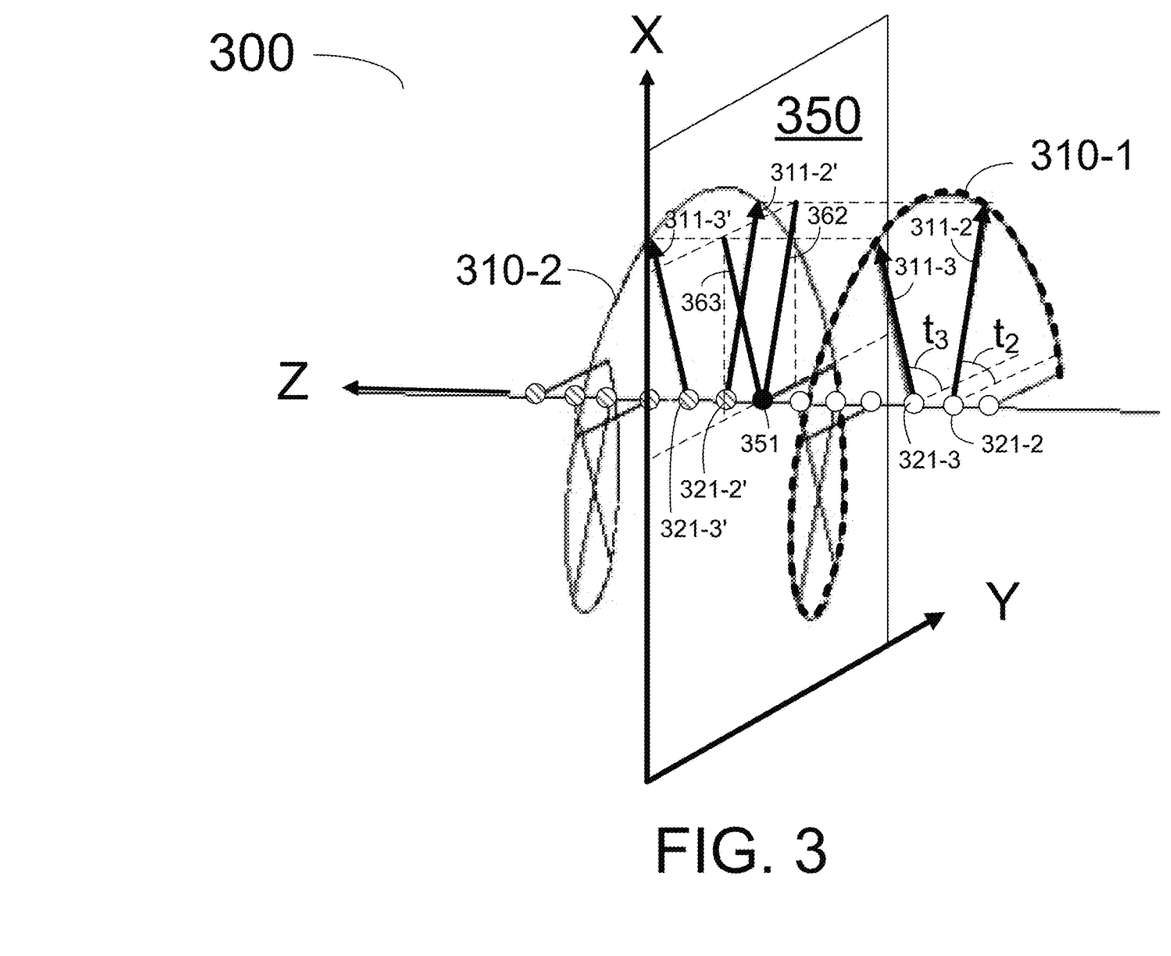
FIG. 3 is a graphical representation of an IVUS scan and a reconstruction plane according to an embodiment of the present disclosure.

FIG. 3 shows an IVUS scan 300 and a reconstruction plane 350 according to an embodiment of the present disclosure. FIG. 3 illustrates consecutive frames 310-1 and 310-2. Frame 310-1 includes A-scan lines 311-2 and 311-3, and frame 310-2 includes A-scan lines 311-2' and 311-3'. A-scan line 311-2 forms an angle $t_2$ about the z-axis, and has a first point 321-2 on the z-axis. A-scan line 311-3 forms an angle $t_3$ about the z-axis, and has a first point 321-3 on the z-axis. A-scan line 311-2' forms an angle $t_2$ about the z-axis, and has a first point 321-2' on the z-axis. A-scan line 311-3' forms an angle $t_3$ about the z-axis, and has a first point 321-3' on the z-axis. Reconstruction plane 350 includes reconstructed scan lines 362 and 363. In some embodiments, reconstructed scan line 362 is formed by interpolation of A-scan line 311-2 and A-scan line 311-2'. Likewise, reconstructed scan line 363 may be formed by interpolation of A-scan line 311-3 and A-scan line 311-3'. Interpolation of A-scan lines as described may use function $f_z$ such as given by Equation 1, above.

According to some embodiments, reconstruction plane 350 may be located at the transition between the end of frame 310-1 and the beginning of frame 310-2. In some embodiments, reconstruction plane 350 may include point 351, at the beginning of frame 310-2. According to some embodiments, reconstruction plane 350 may include polar data (r, θ) and then the polar data may be converted into raster scan, x/y data. Such embodiments may be used in conjunction with processing steps that are conveniently performed with polar data, such as blood speckle reduction. In some embodiments, data interpolation may be included with raster scan conversion, reducing the number of steps in image reconstruction.

According to some embodiments, reconstruction plane 350 including point 351 interpolates data from frame 310-1 and data from frame 310-2. Using function $f_z$ from Equation 1, a coplanar image may be reconstructed at a plane 350 substantially orthogonal to the z-direction. For example, a set of gray values $g_1$, and $g_2$, may be obtained from data points 1 and 2 having z-coordinates $z_1$ and $z_2$, respectively. For simplicity of illustration, it may be assumed that $z_1 < z_2$. Thus, data point 2 may be proximal relative to point 1, according to the coordinate axis selected in FIG. 1. For a point in reconstruction plane 350 having a $z_0$ coordinate, where $z_1 < z_0 < z_2$, the gray scale intensity, $g_0$, may be obtained by a linear equation interpolating the set of values $(z_1, g_1)$ and $(z_2, g_2)$ as $$\frac{g_0 - g_1}{z_0 - z_1} = \frac{g_2 - g_1}{z_2 - z_1}$$

Thus, a gray value $g_0$ at position $z_0$ is given by $$g_0 = g_1 + \frac{z_0 - z_1}{z_2 - z_1}(g_2 - g_1) \quad (2)$$

For data point 1 identified by polar indices $i_r$ and $i_\theta$ at frame index $i_z$, the value of $z_1$ may be provided by function $f_z$ (cf. Equation 1)

$$z_1 = f_z(i_r; i_\theta; i_z);$$

In some embodiments, data point 2 may be identified by the same polar indices $i_r$ and $i_\theta$ as data point 1, and frame index $i_z+1$. Thus, coordinate $z_2$ may be provided by function $f_z$ as follows $$z_2 = f_z(i_r; i_\theta; i_z+1)$$

A point in reconstruction plane 350 may have a z-coordinate $z_0$ equal to that of point 351, having indices $i_r=0$, $i_\theta=0$, and $i_z+1$. Thus, $z_0$ may be provided by function $f_z$ as $$z_0 = f_z(0;0;i_z+1)$$

If we select reconstruction plane 350 to include a first point 351 in a scan frame such as frame 310-2, there may be points within reconstruction plane 350 that belong to proximal frame 310-2. For such points, no interpolation is necessary and the corresponding gray scale intensity in reconstruction plane 350 may be as measured during the IVUS scan. In some embodiments, points in reconstruction plane 350 may have $(r,\theta)$ coordinates matching the $i_r$ and $i_\theta$ indices of a point 1 in distal frame 310-1 and matching the $i_r$ and $i_\theta$ indices of a point 2 in proximal frame 310-2. For such points in reconstruction plane 350, a gray value may be associated, as follows. From Equations 1 and 2, and the above definitions of $z_0$, $z_1$, and $z_2$, the following relation may be formed $$\frac{z_0 - z_1}{z_2 - z_1} = \frac{\frac{i_z+1}{\omega_s} - \frac{1}{\omega_s}\left(i_z + \frac{i_\theta}{n_\theta}\right) - i_r \Delta t_r}{\frac{1}{\omega_s}\left(i_z + 1 + \frac{i_\theta}{n_\theta}\right) + i_r \Delta t_r - \frac{1}{\omega_s}\left(i_z + \frac{i_\theta}{n_\theta}\right) - i_r \Delta t_r}$$

$$= \frac{i_z + 1 - i_z - \frac{i_\theta}{n_\theta} - i_r \Delta t_r \omega_s}{i_z + 1 + \frac{i_\theta}{n_\theta} + i_r \Delta t_r \omega_s - i_z - \frac{i_\theta}{n_\theta} - i_r \Delta t_r \omega_s}$$

$$= 1 - \frac{i_\theta}{n_\theta} + i_r \Delta t_r \omega_s$$

We note that the above relation is independent of $v_z$ and $i_z$, and may be computed only once for each polar coordinate pair $(i_r; i_\theta)$. In some embodiments, indices $(i_r; i_\theta)$ are associated with a polar coordinate pair $(r,\theta)$ as described in detail above (cf. FIG. 2). In some embodiments, a coefficient matrix, C, for indices $(i_r; i_\theta)$ may be formed as follows $$C(i_r, i_\theta) = 1 - \frac{i_\theta}{n_\theta} - i_r \Delta t_r \omega_s \quad (3)$$

Accordingly, coefficient matrix C may be formed from instrument parameters and the specific IVUS scan configuration, prior to the start of a scan. Coefficient matrix C may be applied for interpolations along the z-axis regardless of the specific value of the z-coordinate for reconstruction plane 350. Thus, in some embodiments Equation 2 may be modified to read $$g_0 = g_1 + C(i_r, i_\theta) \cdot (g_2 - g_1)$$

Gray values $g_1$ and $g_2$ may be the gray values measured for point 1 and point 2 in IVUS scan frames 310-1 and 310-2, having indices $(i_r; i_\theta; i_z)$ and $(i_r; i_\theta; i_z+1)$ respectively. A function $I'_p(i_r; i_\theta; i_z)$ providing measured gray values at polar indices $(i_r; i_\theta; i_z)$, may be formed such that $$g_1 = I'_p(i_r; i_\theta; i_z)$$

and $$g_2 = I'_p(i_r; i_\theta; i_z+1).$$

Thus, an interpolated value for the gray scale $I_p(i_r; i_\theta; i_z)$ reconstruction plane 350 at the beginning of frame $i_z+1$ may be formed as $$I_p(i_r, i_\theta, i_z) = I'_p(i_r, i_\theta, i_z) + C(i_r, i_\theta) \cdot (I'_p(i_r, i_\theta, i_z+1) - I'_p(i_r, i_\theta, i_z)) \quad (4)$$

According to embodiments disclosed herein, Equation 4 may be the same, regardless of the specific value of pullback velocity $v_z$. Thus, embodiments such as disclosed herein provide a coplanar image in reconstruction plane 350 by interpolating gray values from consecutive collection frames 310-1 (distal) and 310-2 (proximal). For example, in some embodiments a coplanar image in polar coordinates is formed such that reconstruction plane 350 is located at the beginning of proximal frame 310-2. This means that $I_p$ can be computed for almost all IVUS scan frames. In some embodiments the last z-position of transducer 150 corresponding to the highest $i_z$ value of the IVUS scan may not have a reconstruction plane 350 associated with it. In some embodiments, interpolated values $I_p(i_r; i_\theta; i_z)$ for a coplanar image in reconstruction plane 350 may replace the stored frame values $I'_p(i_r; i_\theta; i_z)$ that is no longer needed, thus no extra memory is needed to store the corrected data.

Figure 4:
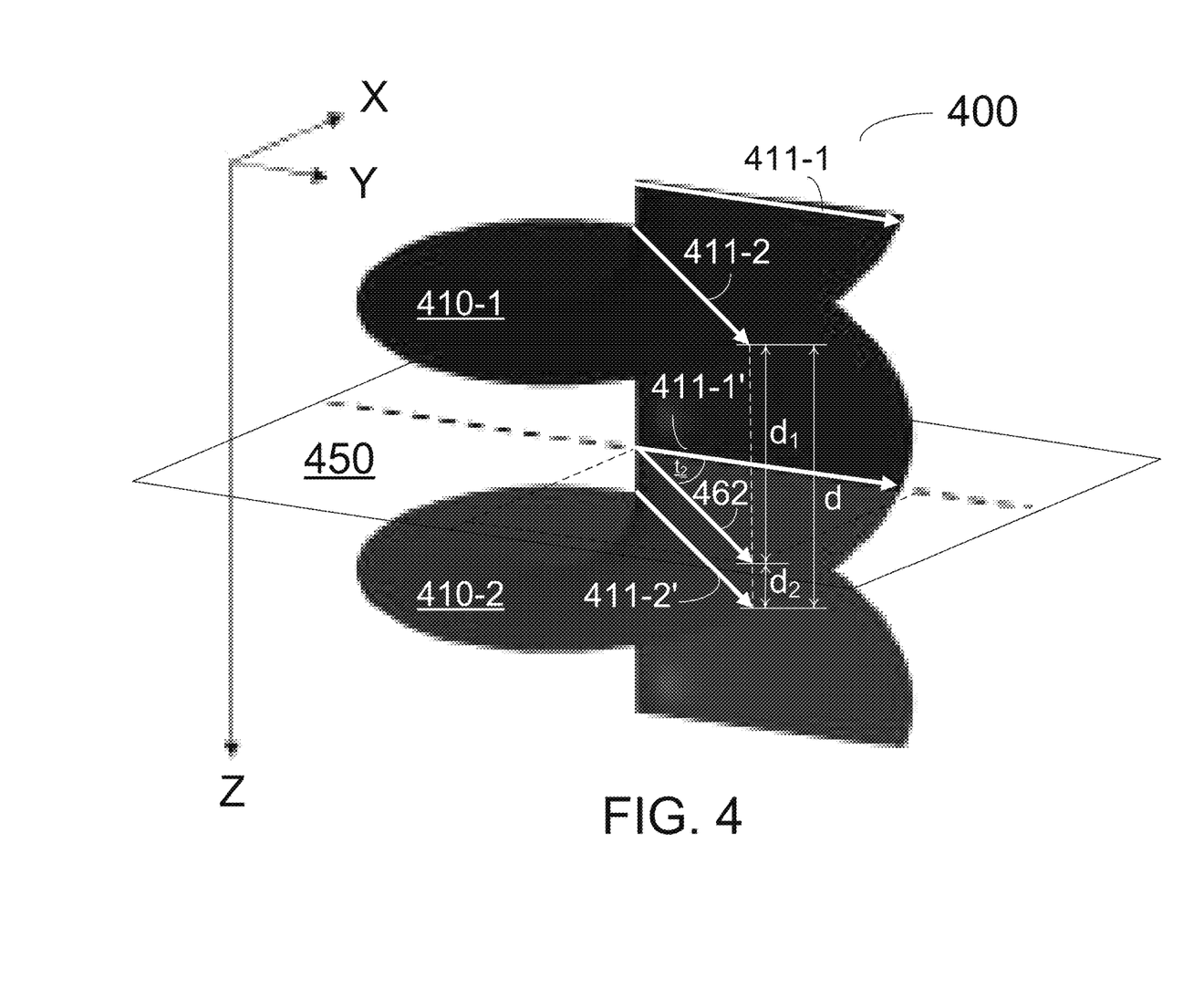
FIG. 4 is a graphical representation of an IVUS scan and a reconstruction plane according to an embodiment of the present disclosure.

FIG. 4 shows an IVUS scan 400 and a reconstruction plane 450 according to another embodiment of the present disclosure. Similarly to what has been described above in relation to FIGS. 2 and 3, scan 400 includes distal frame 410-1, adjacent to proximal frame 410-2. Also shown in FIG. 4 is a first A-scan line 411-1 in frame 410-1, and a first A-scan line 411-1' in frame 410-2. For illustration purposes, coordinate system XYZ in FIG. 4 is chosen so that the Y-axis points along the direction of A-scan lines 411-1 and 411-1'. As the catheter moves with velocity $v_z$ along the z-axis (down, in FIG. 4), A-scan lines define a helical trajectory, rotating clockwise. Each A-scan line forms an angle $t_2$ about the z-axis, measured from the Y-axis. Reconstruction plane 450 includes reconstructed scan line 462. In some embodiments, reconstructed scan line 462 is formed by interpolation of A-scan line 411-2 and A-scan line 411-2'. In some embodiments, interpolation of A-scan lines 411-2 and 411-2' may include using function $f_z$ (cf. Equation 1). In some embodiments, interpolation of A-scan lines 411-2 and 411-2' may include using relative distances between reconstruction plane 450 and A-scan line 411-2 ($d_1$), and A-scan line 411-2' ($d_2$).

In typical IVUS imaging, the time interval between two consecutive frames (frame time interval, $\Delta t_z$) is much larger than the time interval between subsequent angular samplings (angular time interval, $\Delta t_\theta$), or A-scan lines. The time interval between two consecutive A-scan lines ($\Delta t_\theta$) is also much larger than the time interval between the acquisition of subsequent radial samples (radial time interval, $\Delta t_r$). In some examples, the frame time interval is at least an order of magnitude greater than the angular time interval and the angular time interval is at least an order of magnitude greater than the radial time interval.

$$\Delta t_z >> \Delta t_\theta >> \Delta t_r.$$

For example, for a 30 fps frame rate image with 256 scan lines sampled at 40 MHz:

$$\Delta t_z = 1/30 \text{ fps} = 3.3 \times 10^{-2} \text{ s} >> \Delta t_\theta = 1/30 \text{ fps}/256 = 1.3 \times 10^{-4} \text{ s} >> \Delta t_r = 1/40 \text{ MHz} = 2.5 \times 10^{-8} \text{ s}.$$

Accordingly, the specific values shown above are illustrative only, and not limiting. For example, time interval $\Delta t_z$ may have any value between a few milliseconds (ms) and a few hundreds of microseconds (μs). Time interval $\Delta t_\theta$ may have any value between a few hundreds of μs and a few hundreds of nanoseconds (ns). Time interval $\Delta t_r$ may have any value below a few hundreds of nanoseconds (ns).

In some embodiments seam lines may be removed in coplanar image reconstruction as an additional step on top of the existing single-frame scan-conversion routine. Preserving reconstructed scan-lines in a coplanar frame in polar coordinates prior to scan-conversion allows use of processing routines such as border detection that benefit from polar data. Further processing routines may use standard 2D interpolation of the reconstructed, coplanar data in r and θ directions, according to embodiments described above.

In FIG. 4 the coplanar image in reconstruction plane 450 may be interpolated using a weighted average between data in frame 410-1 and data in frame 410-2. For example, for reconstructed scan line 462 an interpolation procedure may use a first weight factor fac1=($d_1$/d) for A-scan line 411-2' in the proximal frame, and a second weight factor fac2=($d_2$/d)=1−(d1/d) for A-scan line 411-2 in the distal frame. If we assume the pullback velocity and rate of rotation to be constant, then reconstructed scan-lines may be formed on the coplanar frame for all or almost all directions $t_2$ used in A-scan lines for a given IVUS collection frame. In some embodiments, the value of fac1 and fac2 may be derived from the scan-line number $i_\theta$ relative to the total number of scan-lines $n_\theta$, as follows:

$$I_p(i_r; i_\theta; i_z) = \frac{i_\theta}{n_\theta} \cdot I'_p(i_r; i_\theta; i_z) + \left(1 - \frac{i_\theta}{n_\theta}\right) \cdot I'_p(i_r; i_\theta; i_z + 1), \quad (5)$$

where $$fac1 = \frac{i_\theta}{n_\theta},$$

and $$fac2 = 1 - \frac{i_\theta}{n_\theta}.$$

According to some embodiments, Equation 5 is a combination of Equations 3 and 4 with the term $i_r \cdot \Delta t_r \cdot \omega_s$ neglected. This may be used in embodiments where $\Delta t_z \gg \Delta t_\theta \gg \Delta t_r$. In Equation 5, $I'_p(i_r; i_\theta; i_z)$ represents a gray scale measurement for a data point from an A-scan line of distal frame 410-1. And $I'_p(i_r; i_\theta; i_z+1)$ represents a gray scale measurement for a data point of proximal frame 410-2.

Figure 5:
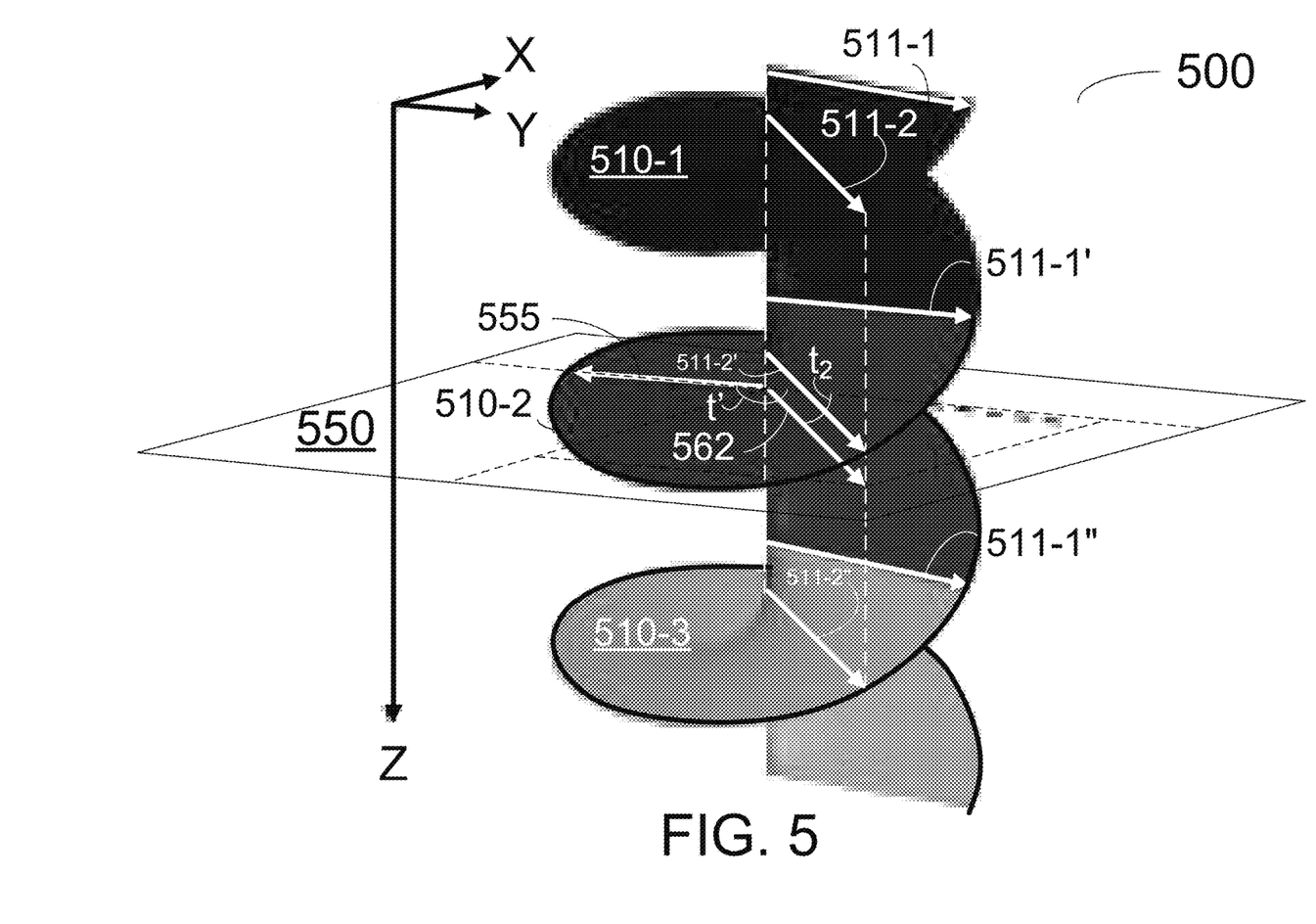
FIG. 5 is a graphical representation of an IVUS scan and a reconstruction plane according to an embodiment of the present disclosure.

FIG. 5 shows an IVUS scan 500 and a reconstruction plane 550 according to an embodiment of the present disclosure. FIG. 5 illustrates a sequence of three IVUS scan frames 510-1 (distal), 510-2 (middle), and 510-3 (proximal). FIG. 5 also illustrates a first A-scan line 511-1 in frame 510-1, a first A-scan line 511-1' in frame 510-2, and a first A-scan line 511-1" in frame 510-3. Reconstruction plane 550 includes reconstructed scan line 562, forming an angle $t_2$ about the z-axis, measured relative to the Y-axis, as described in detail relation to FIGS. 2, 3, and 4 above. Reconstruction plane 550 also includes A-scan line 555 from frame 510-2, forming a polar angle t'=180° with the Y-axis. According to some embodiments, reconstructed scan line 562 may be obtained from interpolation of a first A-scan line from middle frame 510-2, and a second A-scan line selected from either distal frame 510-1, or proximal frame 510-3. In some embodiments, the second A-scan line selected for interpolation belongs to proximal frame 510-3 when reconstruction plane 550 is proximal to the first A-scan line for interpolation. In some embodiments, the second A-scan line selected for interpolation belongs to distal frame 510-1, when reconstruction plane 550 is distal to the first A-scan line for interpolation.

For example, in the configuration illustrated in FIG. 5, scan line 562 is interpolated from a first A-scan line 511-2' in frame 510-2. Plane 550 is proximal to A-scan line 511-2'; thus, the second A-scan line for interpolation is A-scan line 511-2" in proximal frame 510-3. According to some embodiments, the selection of a second A-scan line for interpolation from either distal frame 510-1 or proximal frame 510-3 depends on the polar angle $t_2$ of reconstructed scan line 562, relative to the polar angle t' where the interpolated coplanar frame intersects with the helical frame 510-2. Thus, in some embodiments, when angle $t_2$ is smaller than angle t' the second A-scan line is selected from distal frame 510-1. In some embodiments, when angle $t_2$ is larger than angle t', the second A-scan line is selected from proximal frame 510-3.

In FIG. 5, a number $i'_\theta$ may be defined as scan-line index of middle frame 510-2, at the line formed by the intersection of middle frame 510-2 with reconstruction frame 550. Value $i'_\theta$ can be a fractional value because it may not coincide with a collected A-scan-lines of frame 510-2. In FIG. 5 the intersection includes A-scan line 555 at 180° from A-scan line 511-1. Thus, an interpolation equation for gray scale value $I_p$ at a point defined by polar indices ($i_r$, $i_\theta$) in reconstruction plane 550 may be as $$I_p(i_r, i_\theta, i_z) = \quad (6)$$

$$\begin{cases} \left(0.5 + \frac{i_\theta}{n_\theta}\right) \cdot I'_p(i_r, i_\theta, i_z) + \left(0.5 - \frac{i_\theta}{n_\theta}\right) \cdot I'_p(i_r, i_\theta, i_z + 1); i_\theta \leq i'_\theta \\ \left(1.5 - \frac{i_\theta}{n_\theta}\right) \cdot I'_p(i_r, i_\theta, i_z) + \left(\frac{i_\theta}{n_\theta} - 0.5\right) \cdot I'_p(i_r, i_\theta, i_z - 1); i_\theta > i'_\theta \end{cases}$$

In Equation 6 reconstruction plane 550 is defined by the index $i_z$ of middle frame 510-2. In some embodiments, a plurality of coplanar reconstruction frames may be formed from frames 510-1, 510-2, and 510-3, having multiple intersection lines with middle frame 510-2. For each reconstruction plane that intersects with frame 510-2, an intersection line may form a polar angle $i'_\theta$ with the Y-axis. In such embodiments the display frame rate is effectively increased by including a plurality of reconstruction planes formed from three consecutive scan frames 510-1, 510-2, and 510-3. So, for any arbitrary angle ($i'_\theta$) of intersection between a reconstruction plane 550 and helical frames, the interpolation equation for gray scale value $I_p$ at a point defined by polar indices ($i_r$, $i_\theta$) in reconstruction plane 550 may be:

$$I_p(i_r, i_\theta, i_z) = \quad (7)$$

$$\begin{cases} \left(1 - \frac{i'_\theta}{n_\theta} + \frac{i_\theta}{n_\theta}\right) \cdot I'_p(i_r, i_\theta, i_z) + \left(\frac{i'_\theta}{n_\theta} - \frac{i_\theta}{n_\theta}\right) \cdot I'_p(i_r, i_\theta, i_z + 1); i_\theta \leq i'_\theta \\ \left(1 + \frac{i'_\theta}{n_\theta} - \frac{i_\theta}{n_\theta}\right) \cdot I'_p(i_r, i_\theta, i_z) + \left(\frac{i_\theta}{n_\theta} - \frac{i'_\theta}{n_\theta}\right) \cdot I'_p(i_r, i_\theta, i_z - 1); i_\theta > i'_\theta \end{cases}$$

Figure 6:
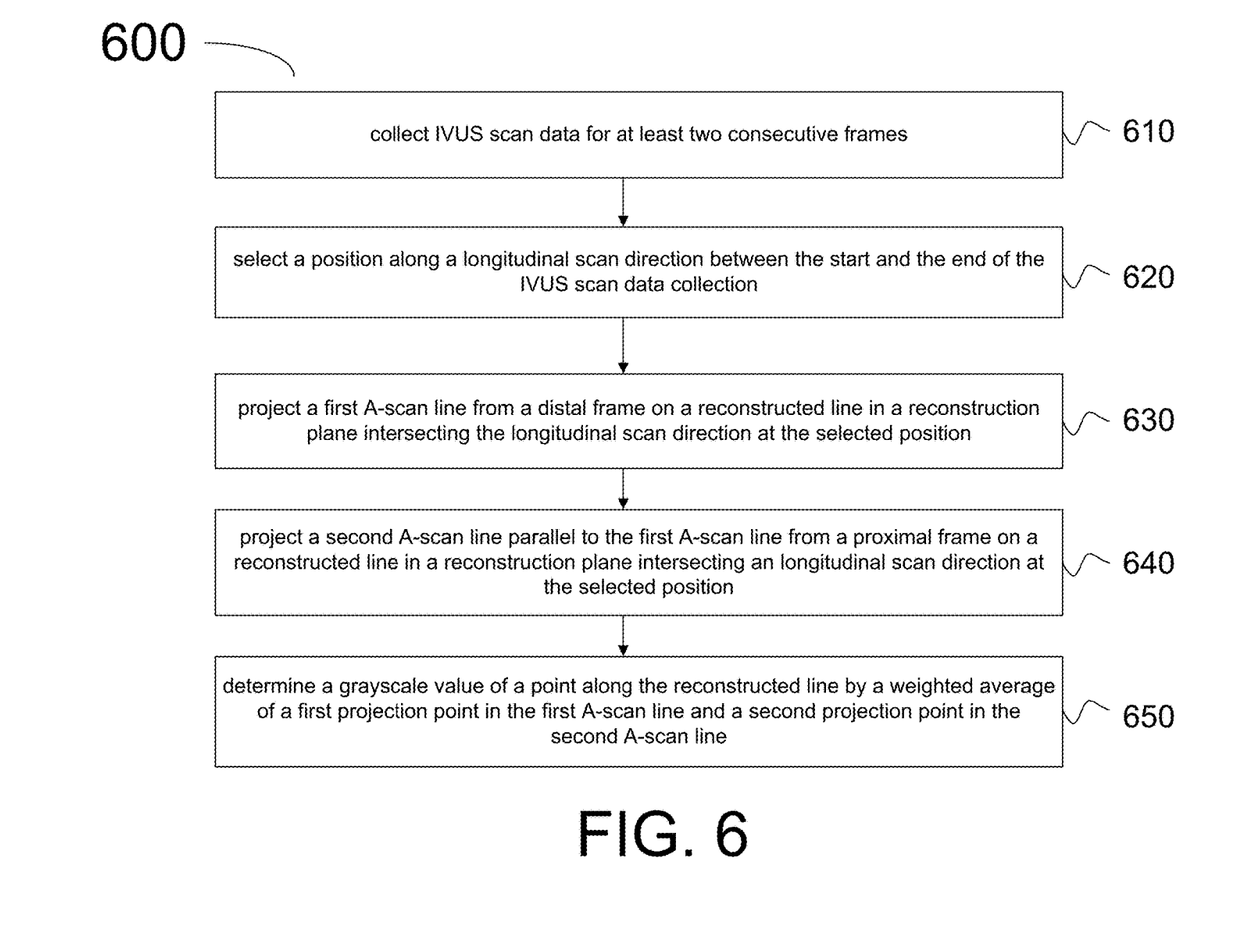
FIG. 6 shows a flow chart of a method for reconstructing a coplanar image in an IVUS scan according to an embodiment of the present disclosure.

FIG. 6 shows a flow chart of a method 600 for reconstructing an image plane in an IVUS scan, according to an embodiment of the present disclosure. According to some embodiments, method 600 may be performed by console 106 using processor circuit 116 and memory circuit 117 and/or PIM 104 using processor circuit 114 and memory circuit 115 based on scan data provided by transducer 150

(cf. FIG. 1). In some embodiments, some steps in method 600 may be performed by console 106 and some steps in method 600 may be performed by PIM 104. The reconstructed image plane in method 600 may be provided to a user in display 108.

In step 610 IVUS scan data for at least two consecutive frames are collected. In step 620 a position along a longitudinal scan direction is selected between the start and the end of the IVUS scan data collection. In step 630 a first A-scan line is projected from a distal frame on a reconstructed line in a reconstruction plane intersecting the longitudinal scan direction at the selected position. In step 640 a second A-scan line parallel to the first A-scan line is projected from a proximal frame on a reconstructed line in a reconstruction plane intersecting a longitudinal scan direction at the selected position. In step 650 a grayscale value of a point along the reconstructed line is determined. In some embodiments, step 650 includes using a weighted average of a first position point in the first A-scan line and a second position point in the second A-scan line.

Figure 7:
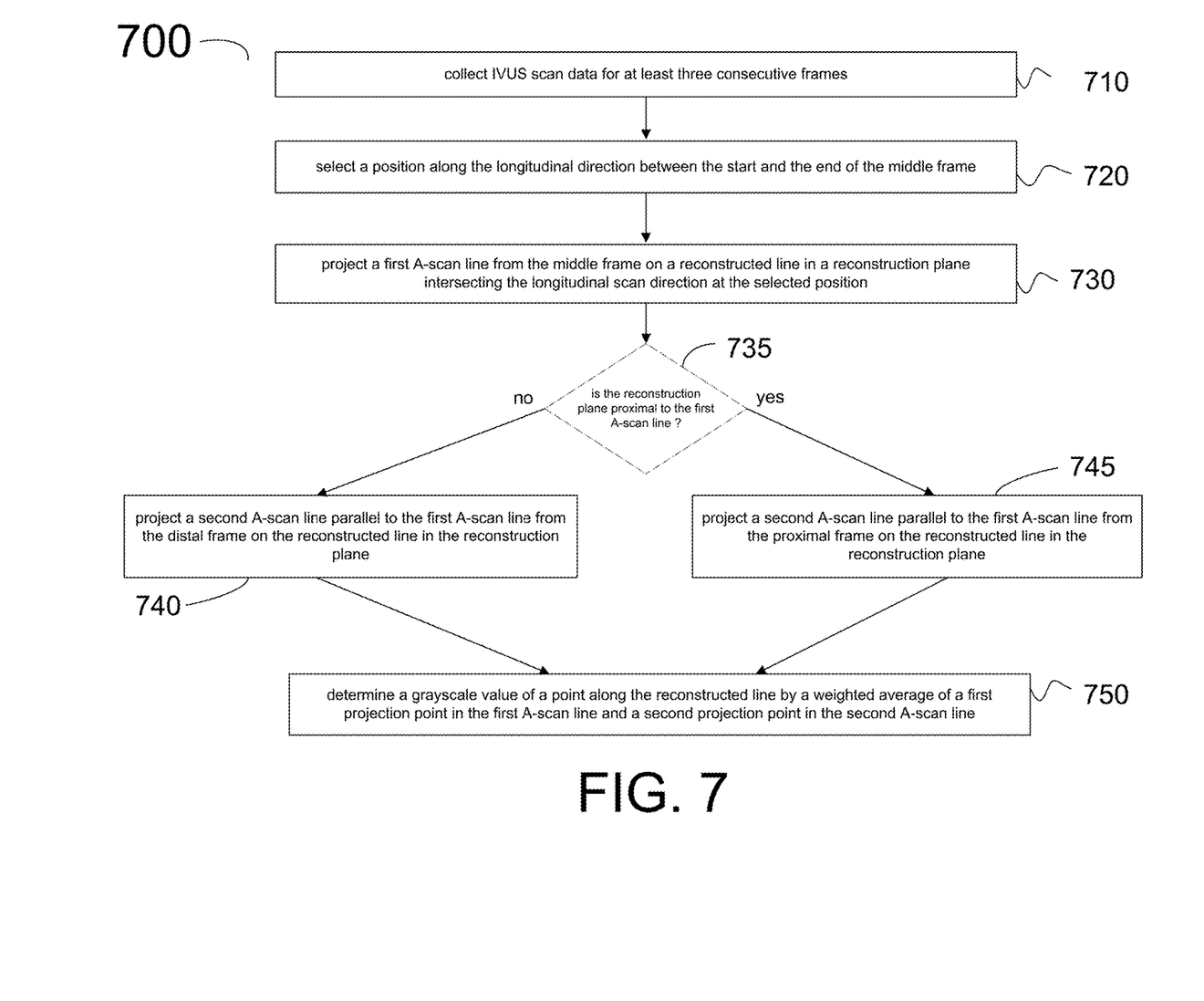
FIG. 7 shows a flow chart of a method for reconstructing a coplanar image in an IVUS scan according to an embodiment of the present disclosure.

FIG. 7 shows a flow chart of a method 700 for reconstructing an image plane in an IVUS scan, according to an embodiment of the present disclosure. According to some embodiments, method 700 may be performed by console 106 using processor circuit 116 and memory circuit 117 and/or PIM 104 using processor circuit 114 and memory circuit 115 based on scan data provided by transducer 150 (cf. FIG. 1). In some embodiments, some steps in method 700 may be performed by console 106 and some steps in method 700 may be performed by PIM 104. The reconstructed image plane in method 700 may be provided to a user in display 108.

In step 710 IVUS scan data for at least three consecutive frames are collected. For example, a distal frame 510-1, a middle frame 510-2, and a proximal frame 510-3 (cf. FIG. 5). In step 720 a position along a longitudinal scan direction is selected between the start and the end of the second frame, such as frame 510-2 (cf. FIG. 5). In step 730 a first A-scan line is projected from the second frame on a reconstructed line in a reconstruction plane intersecting the longitudinal scan direction at the selected position. In step 735 it is queried whether the reconstruction plane is proximal or distal to first A-scan line. If the reconstruction plane is proximal to the first A-scan line, step 745 is performed. In step 745 a second A-scan line parallel to the first A-scan line is projected from the proximal frame on the reconstructed line in the reconstruction plane. If the reconstruction plane is not proximal to the first A-scan line, step 740 is performed. In step 740 a second A-scan line parallel to the first A-scan line is projected from the distal frame on the reconstructed line in the reconstruction plane. In step 750 a grayscale value of a point along the reconstructed line is determined. In some embodiments, step 750 includes using a weighted average of a first point in the first A-scan line and a second point in the second A-scan line.

Embodiments of the invention described above are exemplary only. One skilled in the art may recognize various alternative embodiments from those specifically disclosed. Those alternative embodiments are also intended to be within the scope of this disclosure. As such, the invention is limited only by the following claims.

What is claimed is:

1. A method for generating coplanar intravascular (IVUS) images, the method comprising:

obtaining IVUS scan data by an IVUS imaging catheter positioned within a vessel during a pullback of the imaging catheter through the vessel, wherein the IVUS scan data comprises a plurality of A-scan lines arranged in a plurality of helical frames, wherein the pullback extends along a longitudinal axis and has a starting point and an ending point, the ending point being proximal of the starting point;

determining a plurality of reconstruction planes along the longitudinal axis between the starting point and the ending point, wherein each of the plurality of reconstruction planes extends perpendicular to the longitudinal axis, and wherein the plurality of helical frames is not perpendicular to the longitudinal axis;

determining a plurality of grayscale values coplanar with the plurality of reconstruction planes based on the obtained IVUS scan data, wherein, for a respective reconstruction plane, the determining comprises:

projecting first A-scan lines from a helical frame out of the plurality of helical frames distal to the respective reconstruction plane to the respective reconstruction plane;

projecting second A-scan lines from a helical frame out of the plurality of helical frames proximal to the respective reconstruction plane to the respective reconstruction plane, wherein the second A-scan lines are parallel to the first A-scan lines; and determining the grayscale values of the coplanar IVUS image at the respective reconstruction plane as a weighted average of the first A-scan lines and the second A-scan lines; and displaying the plurality of grayscale values coplanar with the plurality of reconstruction planes.

2. The method of claim 1, wherein each of the plurality of helical frames comprises a plurality of A-scan lines radially projected about the longitudinal axis collected at a selected angular time interval and completing a full rotation about the longitudinal axis.

3. The method of claim 2, wherein each of the plurality of A-scan lines comprises a plurality of radial points collected at a selected radial time interval.

4. The method of claim 3, wherein the plurality of helical frames are collected at a selected frame time interval.

5. The method of claim 4, wherein the frame time interval is at least an order of magnitude greater than the angular time interval; and wherein the angular time interval is at least an order of magnitude greater than the radial time interval.

6. The method of claim 1, wherein the frame proximal to the respective reconstruction plane and the frame distal to the respective reconstruction plane are consecutive frames of the IVUS pullback.

7. The method of claim 1, wherein the IVUS pullback is performed at a constant speed.

8. The method of claim 7, wherein a pullback device is utilized to perform the IVUS pullback.

9. The method of claim 1, wherein the IVUS pullback is performed at a non-uniform speed.

10. An intravascular imaging system, comprising:

an intravascular imaging device comprising at least one imaging element;

a processing system in communication with the intravascular imaging device, the processing system configured to:

obtain intravascular scan data from the intravascular imaging device during an intravascular pullback through a vessel, wherein the intravascular scan data comprises a plurality of A-scan lines arranged in a plurality of helical frames, wherein the intravascular pullback extends along a longitudinal axis and has a starting point and an ending point, the ending point being proximal of the starting point, wherein the plurality of helical frames is not perpendicular to the longitudinal axis;

determine a plurality of reconstruction planes along the longitudinal axis between the starting point and the ending point, wherein each of the plurality of reconstruction planes extends perpendicular to the longitudinal axis;

determine a plurality of grayscale values coplanar with the plurality of reconstruction planes based on the obtained scan data for a frame proximal to a respective reconstruction plane of the plurality of reconstruction planes and a frame distal to the respective reconstruction plane; and display, on a display device, the plurality of grayscale values coplanar with the plurality of reconstruction planes.

11. The system of claim 10, wherein the processing system is configured to determine the plurality of grayscale values co-planar with the plurality of reconstruction planes by:

projecting first A-scan lines from the distal frame to the respective reconstruction plane;

projecting second A-scan lines parallel to the first A-scan lines from the proximal frame to the respective reconstruction plane; and determining grayscale values on the respective reconstruction plane by a weighted average of the first A-scan lines and the second A-scan lines.

12. The system of claim 11, wherein the processing system includes a console and the display.

13. The system of claim 12, wherein the processing system further includes a patient interface module (PIM) configured to interface with the intravascular imaging device and the console.

14. The system of claim 11, wherein the intravascular imaging device is an intravascular ultrasound (IVUS) device.

15. The system of claim 14, wherein the IVUS device includes a single ultrasound transducer.

16. The system of claim 14, wherein the IVUS device includes a transducer array.

17. The system of claim 10, wherein the intravascular imaging device is an optical coherence tomography (OCT) device.

18. The system of claim 10, wherein the plurality of grayscale values comprises seamless images.

19. The system of claim 10, wherein determining the plurality of grayscale values coplanar with the plurality of reconstruction planes comprises:

determining grayscale values for a first plurality of points by obtaining grayscale values at the first plurality of points of the frame proximal to the respective reconstruction plane if the frame proximal to the respective reconstruction plane and the respective reconstruction plane intersect at the first plurality of points;

determining grayscale values for a second plurality of points by obtaining grayscale values at the second plurality of points of the frame distal to the respective reconstruction plane if the frame distal to the respective reconstruction plane and the respective reconstruction plane intersect at the second plurality of points; and determining grayscale values for a third plurality of points based on an weighted average of grayscale values of the frame proximal to the respective reconstruction plane and grayscale values of the frame distal to the respective reconstruction plane if the frame proximal to the respective reconstruction plane and the frame distal to the respective reconstruction plane do not intersect the respective reconstruction plane.

\* \* \* \* \*